United States Patent [19]

Blum

[11] 4,336,258

[45] Jun. 22, 1982

[54] DERIVATIVES OF EUGENOL AS MEDICAMENTS

[76] Inventor: Jean Blum, 44-46 rue du Gal Crémer, 92700 Colombes, France

[21] Appl. No.: 190,982

[22] Filed: Sep. 26, 1980

[30] Foreign Application Priority Data

Sep. 27, 1979 [FR] France ................................ 79 24051

[51] Int. Cl.$^3$ .................... A61K 31/44; A61K 31/465; A61K 31/455; C07D 211/90
[52] U.S. Cl. ..................................... 424/263; 424/264; 424/266; 546/322; 546/326
[58] Field of Search ................ 546/322, 326; 424/263, 424/264, 266

[56] References Cited

U.S. PATENT DOCUMENTS 3,876,648  4/1975  Haas et al. .......................... 546/326

OTHER PUBLICATIONS

Charonnot, et al., Bulletin Soc. Chim. Fr., 1947, pp. 339-341.

*Primary Examiner*—John M. Ford
*Assistant Examiner*—Robert C. Whittenbaugh
*Attorney, Agent, or Firm*—McDougall, Hersh & Scott

[57] ABSTRACT

As new medicaments notably in the field of stomatology, the phenolic esters of eugenol and N-heteroaryl carboxylic acids including their N-oxides, and notably eugenyl nicotinate, picolinate and N-oxynicotinate and their pharmaceutical forms are disclosed.

A new long acting form of local antalgesic is disclosed having a resorbable solid or doughy support which is impregnated with the active principle. The support may be for instance made of gelatin sponge.

5 Claims, No Drawings

DERIVATIVES OF EUGENOL AS MEDICAMENTS

This invention relates to the use of particular derivatives of eugenol as medicaments, notably in the field of stomatology.

Eugenol is widely used for its antiseptic and soothing properties, but the effects are fugacious and of low intensity.

It was very surprising to find that the esterification of this phenol by N-heteroaryl carboxylic acids leads to a considerable improvement of its antalgesic properties in such a manner that it is possible to cure efficiently alveolite fits which are incurable by treatment with the most powerfull known antalgics.

Then, this invention concerns as new medicaments, the phenolic esters of eugenol and N-heteroaryl carboxylic acids, including their N-oxides.

This invention relates particularly to the following medicaments for use in stomatology, the nicotinate of eugenol, the N-oxynicotinate of eugenol and the picolinate of eugenol.

The nicotinate of eugenol has been described by R. Charonnat et al. (Bulletin Soc. Chim. Fr. 1947, 339–41) but no therapeutic properties of this compound have been previously reported. In addition, the other derivatives of the present inventions have not been reported in the literature.

In the line of new industrial products, the invention relates to the phenolic esters of eugenol and N-heteroaryl carboxylic acids including their N-oxyderivatives, but not to nicotinic acid itself.

In the line of industrial products the invention relates notably to the N-oxynicotinate and picolinate of eugenol and their process of manufacture.

These new esters of eugenol are obtained by the reaction of eugenol with the chosen N-heteroaryl carboxylic acid or one of its reactive derivatives. For economic reasons the best reactive derivatives of acids are chloride but it may be more advantageous to use other derivatives, for instance a methylester in the case of the N-oxynicotinic acid.

When a halide is used, the condensation may be performed in water or in an organic solvent preferably with a basic material to neutralize the evolved hydrogen halide.

The reaction can be carried out in either cold alkaline water, pyridine or benzene in the presence of a tertiary amine.

The invention is illustrated, but is not restricted, by the following examples:

EXAMPLE 1

Nicotinate of eugenol 5 g of eugenol and 6 g of nicotinic chloride hydrochloride was dissolved in 50 ml of pyridine and the mixture was refluxed for 2 hours then cooled and poured over 500 ml of crushed ice. The mixture was allowed to stand overnight before filtering with suction. The recovered crystals were recrystallized from cyclohexane. The almost colorless crystals had a melting point of 77° C. (Kofler bloc) which corresponds with that described by Charonnat et al.

The hydrochloride, obtained by addition of anhydrous HCl, melted with decomposition at about 120° C. It was not previously described in the literature.

EXAMPLE 2

Picolinate of eugenol 5 g of eugenol was dissolved in 25 ml of a 5% soda solution. The solution was cooled to 0° C. and while maintaining the solution below 5° C., 6 g of picolinic chloride hydrochloride was added with vigorous stirring. The solution was allowed to stand for 30 minutes with stirring and was filtered by suction. The recovered product was recrystallized from cyclohexane to yield colorless crystals (m.p. 97° C. Kofler bloc).

EXAMPLE 3

N-oxynicotinate of eugenol 1.39 g of N-oxynicotinic acid was suspended in 20 ml of benzene and 10 ml of thionyl chloride was added slowly. The solution was refluxed with stirring for 30 minutes and evaporated to dryness. Thereafter 20 ml of benzene was added and the solution was again evaporated to dryness. This operation was repeated to eliminate any residual thionyl chloride.

20 ml of benzene was added and 1.64 of eugenol dissolved in 5 ml of benzene and 1.1 ml of triethylamine was added slowly. The solution was refluxed for 15 minutes and triethylamine hydrochloride was separated by filtration. The filtrate was evaporated to dryness and a 5% sodium bicarbonate solution was added to adjust the pH to 8. An oil separated which rapidly crystallized. The product was filtered by suction and was recrystallized from cyclohexane.

The recovered colorless crystals melted first at 123° C., then crystallized and melted again definitely at 133°–134° C.

The same product can also be obtained by transesterification of methyl N-oxynicotinate and eugenol upon heating at about 100° C. for 2 hours equimolar quantities of both substances in dimethylformamide.

The centesimal analysis in C N H and the I.R. spectra of the new esters of eugenol agree with the assigned structures.

To illustrate the pharmacological properties of the esters of the invention, the following properties of the nicotinate of eugenol (NE) are given as an example.

NE was administered to male SWISS, EOPS mice weighing 18 to 20 g. The observed LD 50 of NE was 4,600±320 mg/kg. This lack of oral toxicity was confirmed by intraperitoneal administration; no death occurred at 200 mg/kg.

As reported by Irwintest (psychopharmacologia 13, 222–7, 1968), NE was shown ineffective upon reflexes, comportment and motor stimulation. It shows neither cataleptic, neuroleptic nor antalgic activity when administered to the rear leg of a rat.

NE has a minimal hypocholesterolemic activity at 200 mg/kg in the triton test without any estrogenic activity.

In vitro, NE is slightly antifongic as it somewhat inhibits aggregation of plaquets induced by collagen.

In stomatology NE has noticeable properties as illustrated by the following data.

NE was given in the form of a colorless powder with an acceptable taste. It must be introduced into the alveole or cystic cavity after the surgeon's intervention at a 250 mg dose. It mixes with the blood clot and holds for about a week. Twelve days after application NE is completely resorbed. Other pharmaceuticals, such as antibiotics or anti-inflammatories, can be administered with NE but they are not necessary since NE is thoroughly active when pure, and co-administered drugs may induce undesirable side-effects including: NE is an excellent "anti-pain" agent and notably used after:

304 simple tooth extractions,
162 surgical extractions of the 3d molar,
34 extractions of included canines,
47 extractions during the inflammatory period,
21 ablations of large cysters of tooth origin,
19 conditions of aphthous or ulcerated stomatitis.

In this occurrence the powder itself was used, but a topical solution may be used.

A general and very strong decrease of the postoperative pain was observed in all cases and in 40% of the cases the pain disappeared completely.

A general decrease of postoperative accidents of the alveolite type was also observed. It must be remembered that these accidents occur very often after extraction of the teeth of the inferior maxillary. The patient is overcome during a fortnight by a pain which is not soothed by any known antalgic, not even morphine, and which may be accompanied by sympathetic auditory, ocular and sinous troubles. The patient is unable to sleep and often compelled to cease all activity.

If NE is applied after the extraction and remains in the cavity, a slight pang may persist for 4 or 5 days; but in any case the discomfort cannot be compared with the above described pain. Also, in each of the observed cases no insomnia, no loss of activity, no sympathetic troubles or anorexia were observed.

NE soothes also rapidly the pain in the cases of aphthous stomatitis, which is the formation of tiny ulcers or canker sores in the mucosa of the mouth.

This invention also relates to the pharmaceutical forms for human or veterinary administration of the new medicaments of the invention. The active preparations may be administered by oral, rectal or parental ways, but the local way in the form of tooth-solution, lotion, pomade, powder, paste or the like is preferred.

NE is to be applied directly on the accidental or surgical wound or on mucous membrane and it must remain in place for several days or weeks without further intervention. To satisfy this necessity, the invention relates also a new long acting pharmaceutical form called here under "long acting local form" which consists in impregnating a solid or doughy support which resorbs slowly in the organism with the active principle or ingredient being a pure solid or in solution.

To illustrate this embodiment of the present invention the resorbable support may be a gel or gelatin sponge, an oxidized cellulose gauze or a fibrine wadding.

As the support resorbs itself it releases slowly the active pharmaceuticals as analgesics, antiseptics, antibiotics or the like.

The invention relates notably to the "long acting local forms" in the sponge form and particularly those made of gelatin.

The invention relates also tooth solutions, pastes, powders and impregnated gelatin sponges with NE being in the pure form of mixed with other substances.

New experiments are in course and when using gelatin sponges impregnated with NE it was possible to decrease the effective dose from 250 to 100 mg. It is very easy for the dentist to put the medicament in the proper place and be sure that NE will diffuse slowly and regularly during the cicatrization or healing of the wound.

I claim:

1. A compound consisting of the eugenol ester of N-oxynicotinic acid.

2. A pharmaceutical preparation for the treatment of stomatological disorders comprising a support and between 100 and 250 milligrams of a medicament impregnated on said support, said medicament comprising a eugenol ester of N-oxynicotinic acid.

3. A preparation as defined in claim 2 wherein the support has a sponge structure.

4. A preparation as defined in claim 2 wherein the support is a sponge-like support selected from the group consisting of gelatin, oxidized cellulose and fibrine.

5. A method for the treatment of stomatological disorders comprising the step of applying between 100 and 250 milligrams of a pharmaceutically acceptable ester of eugenol and N-oxynicotinic acid.

* * * * *